(12) United States Patent
Oren et al.

(10) Patent No.: US 9,713,463 B2
(45) Date of Patent: Jul. 25, 2017

(54) TOGGLE BOLT ASSEMBLY AND METHOD OF ASSEMBLY

(75) Inventors: Ran Oren, Kibbutz Gaaton (IL); Eran Zakai, Misgav (IL); Elad Rash, Beit Lehem Haglilit (IL)

(73) Assignee: Howmedica Osteonics Corp, Mahwah, NJ (US)

( * ) Notice: Subject to any disclaimer, the term of this patent is extended or adjusted under 35 U.S.C. 154(b) by 397 days.

(21) Appl. No.: 13/182,851

(22) Filed: Jul. 14, 2011

(65) Prior Publication Data
US 2012/0180291 A1 Jul. 19, 2012

Related U.S. Application Data

(60) Provisional application No. 61/432,481, filed on Jan. 13, 2011.

(51) Int. Cl.
B21D 39/00 (2006.01)
B23P 11/00 (2006.01)
B23P 19/02 (2006.01)
B65D 63/06 (2006.01)
A61B 17/04 (2006.01)

(52) U.S. Cl.
CPC .. *A61B 17/0401* (2013.01); *A61B 2017/0404* (2013.01); *A61B 2017/045* (2013.01); *A61B 2017/0409* (2013.01); *A61B 2017/0414* (2013.01); *A61B 2017/0417* (2013.01); *Y10T 29/49826* (2015.01)

(58) Field of Classification Search
CPC ........ A61B 17/0401; A61B 2017/0404; A61B 2017/0414; A61B 2017/0417; A61B 2017/045; A61B 2017/0409; Y10T 29/49826

USPC ...... 29/525, 525.01, 525.02, 525.03, 525.04, 29/525.13; 606/232, 144, 143; 623/2.36; 248/499, 500, 505, 506
See application file for complete search history.

(56) References Cited

U.S. PATENT DOCUMENTS

| | | | |
|---|---|---|---|
| 860,636 A | 7/1907 | Church | |
| 2,485,531 A | 10/1949 | Dzus et al. | |
| 3,332,118 A | 7/1967 | Temple et al. | |
| 3,976,079 A | 8/1976 | Samuels et al. | |

(Continued)

FOREIGN PATENT DOCUMENTS

WO 2006/130693 A2 12/2006

OTHER PUBLICATIONS

Case No. 2:07-CV-335-TJW, Doc. 82, *Smith & Nephew, Inc.* v. *Arthrex, Inc.*, Infringment of U.S. Pat. No. 5,306,301 and 5,645,588, 47 pages, Nov. 20, 2009.

(Continued)

*Primary Examiner* — Sarang Afzali
*Assistant Examiner* — Darrell C Ford
(74) *Attorney, Agent, or Firm* — Lerner, David, Littenberg, Krumholz & Mentlik, LLP

(57) ABSTRACT

The present invention includes a method of assembling an anchor for use in tissue comprising an anchor body, a continuous closed suture loop and an insert, the method comprising positioning a portion of the continuous closed suture loop through an opening in the anchor body; positioning the insert adjacent the portion of the continuous closed suture loop which was passed through the opening; and securing the insert to the anchor body such that the continuous closed suture loop is secured to the anchor body by the insert.

27 Claims, 7 Drawing Sheets

(56) References Cited

U.S. PATENT DOCUMENTS

| | | | |
|---|---|---|---|
| 4,075,924 A | 2/1978 | McSherry et al. | |
| 4,265,231 A | 5/1981 | Scheller, Jr. et al. | |
| 4,294,156 A | 10/1981 | McSherry et al. | |
| 4,298,298 A | 11/1981 | Pontone | |
| 4,439,079 A | 3/1984 | Losada | |
| 4,590,928 A | 5/1986 | Hunt et al. | |
| 4,650,386 A | 3/1987 | McSherry et al. | |
| 4,782,451 A | 11/1988 | Mazzarella et al. | |
| 5,002,546 A | 3/1991 | Romano | |
| 5,030,219 A | 7/1991 | Matsen, III et al. | |
| 5,139,520 A | 8/1992 | Rosenberg | |
| 5,242,457 A * | 9/1993 | Akopov et al. | 606/144 |
| 5,269,809 A | 12/1993 | Hayhurst et al. | |
| 5,282,832 A * | 2/1994 | Toso | A61B 17/0487 |
| | | | 24/DIG. 50 |
| 5,306,301 A | 4/1994 | Graf et al. | |
| 5,374,269 A | 12/1994 | Rosenberg | |
| 5,395,188 A | 3/1995 | Bailey et al. | |
| 5,409,490 A | 4/1995 | Ethridge | |
| 5,437,677 A | 8/1995 | Shearer et al. | |
| 5,454,821 A | 10/1995 | Harm et al. | |
| 5,464,425 A | 11/1995 | Skiba | |
| 5,484,451 A * | 1/1996 | Akopov et al. | 606/139 |
| 5,496,348 A | 3/1996 | Bonutti | |
| 5,514,159 A * | 5/1996 | Matula | A61B 17/0487 |
| | | | 24/115 H |
| 5,522,846 A | 6/1996 | Bonutti | |
| 5,545,178 A | 8/1996 | Kensey et al. | |
| 5,573,543 A * | 11/1996 | Akopov et al. | 606/144 |
| 5,584,835 A * | 12/1996 | Greenfield | 606/232 |
| 5,628,740 A | 5/1997 | Mullane | |
| 5,645,588 A | 7/1997 | Graf et al. | |
| 5,733,307 A * | 3/1998 | Dinsdale | 606/232 |
| 5,769,894 A | 6/1998 | Ferragamo | |
| 5,868,789 A | 2/1999 | Huebner | |
| 5,921,986 A | 7/1999 | Bonutti | |
| 5,948,002 A | 9/1999 | Bonutti | |
| 6,010,525 A | 1/2000 | Bonutti et al. | |
| 6,045,574 A * | 4/2000 | Thal | 606/232 |
| 6,056,752 A | 5/2000 | Roger | |
| 6,068,648 A | 5/2000 | Cole et al. | |
| 6,099,568 A | 8/2000 | Simonian et al. | |
| 6,110,207 A | 8/2000 | Eichhorn et al. | |
| 6,117,139 A | 9/2000 | Shino | |
| 6,161,999 A | 12/2000 | Kaye et al. | |
| 6,171,310 B1 | 1/2001 | Giordano et al. | |
| 6,187,011 B1 | 2/2001 | Torrie | |
| 6,267,767 B1 | 7/2001 | Strobel et al. | |
| 6,287,065 B1 | 9/2001 | Berlin | |
| 6,419,678 B1 | 7/2002 | Asfora | |
| 6,440,134 B1 | 8/2002 | Zaccherotti et al. | |
| 6,451,030 B2 | 9/2002 | Li et al. | |
| 6,482,210 B1 | 11/2002 | Skiba et al. | |
| RE37,963 E * | 1/2003 | Thal | 606/232 |
| 6,517,542 B1 * | 2/2003 | Papay et al. | 606/232 |
| 6,517,578 B2 * | 2/2003 | Hein | 623/13.13 |
| 6,533,802 B2 * | 3/2003 | Bojarski et al. | 606/232 |
| 6,547,800 B2 * | 4/2003 | Foerster et al. | 606/151 |
| 6,562,071 B2 | 5/2003 | Jarvinen | |
| 6,569,187 B1 | 5/2003 | Bonutti et al. | |
| 6,638,279 B2 | 10/2003 | Bonutti | |
| 6,641,596 B1 * | 11/2003 | Lizardi | 606/232 |
| 6,641,597 B2 * | 11/2003 | Burkhart et al. | 606/232 |
| 6,652,563 B2 * | 11/2003 | Dreyfuss | 606/232 |
| 6,736,829 B1 | 5/2004 | Li et al. | |
| 6,773,436 B2 | 8/2004 | Donnelly et al. | |
| 6,840,953 B2 * | 1/2005 | Martinek | 606/232 |
| 6,923,824 B2 * | 8/2005 | Morgan et al. | 606/232 |
| 7,001,412 B2 * | 2/2006 | Gallagher | A61B 17/0487 |
| | | | 606/151 |
| 7,037,324 B2 | 5/2006 | Martinek | |
| 7,041,120 B2 | 5/2006 | Li et al. | |
| 7,087,073 B2 | 8/2006 | Bonutti | |
| 7,090,690 B2 | 8/2006 | Foerster et al. | |
| 7,097,654 B1 | 8/2006 | Freedland | |
| 7,108,710 B2 * | 9/2006 | Anderson | 606/232 |
| 7,163,540 B2 | 1/2007 | Martello | |
| 7,695,503 B1 * | 4/2010 | Kaiser | A61B 17/0401 |
| | | | 606/300 |
| 7,736,108 B1 | 6/2010 | Bruce et al. | |
| 7,803,173 B2 * | 9/2010 | Burkhart et al. | 606/232 |
| 7,819,898 B2 | 10/2010 | Stone et al. | |
| 7,828,820 B2 * | 11/2010 | Stone et al. | 606/232 |
| 7,875,057 B2 | 1/2011 | Cook et al. | |
| 7,896,907 B2 | 3/2011 | McDevitt et al. | |
| 7,934,506 B2 | 5/2011 | Woodson et al. | |
| 8,109,965 B2 | 2/2012 | Stone et al. | |
| 8,114,127 B2 * | 2/2012 | West, Jr. | 606/232 |
| 8,128,669 B2 | 3/2012 | Bonutti | |
| 8,147,514 B2 | 4/2012 | Bonutti | |
| 8,231,674 B2 | 7/2012 | Albertorio et al. | |
| 8,388,655 B2 * | 3/2013 | Fallin et al. | 606/232 |
| 8,439,946 B2 * | 5/2013 | Miller et al. | 606/232 |
| 8,506,596 B2 * | 8/2013 | Stone et al. | 606/232 |
| 8,591,578 B2 * | 11/2013 | Albertorio et al. | 623/13.13 |
| 8,613,756 B2 * | 12/2013 | Lizardi et al. | 606/232 |
| 8,628,573 B2 * | 1/2014 | Roller et al. | 623/13.14 |
| 8,672,969 B2 * | 3/2014 | Stone et al. | 606/232 |
| 8,840,644 B2 | 9/2014 | Napolitano et al. | |
| 9,510,816 B2 * | 12/2016 | McDevitt | A61B 17/0401 |
| 2001/0025181 A1 | 9/2001 | Freedlan | |
| 2001/0041938 A1 | 11/2001 | Hein | |
| 2002/0015629 A1 | 2/2002 | Ito | |
| 2002/0019634 A1 | 2/2002 | Bonutti | |
| 2002/0183762 A1 * | 12/2002 | Anderson et al. | 606/104 |
| 2003/0135239 A1 | 7/2003 | Gabriel et al. | |
| 2004/0002734 A1 * | 1/2004 | Fallin et al. | 606/232 |
| 2004/0015171 A1 | 1/2004 | Bojarski et al. | |
| 2004/0046009 A1 | 3/2004 | Weisenberg et al. | |
| 2004/0127907 A1 | 7/2004 | Dakin et al. | |
| 2004/0138706 A1 * | 7/2004 | Abrams et al. | 606/232 |
| 2004/0236419 A1 * | 11/2004 | Milo | 623/2.36 |
| 2004/0243128 A1 | 12/2004 | Howland | |
| 2004/0243180 A1 * | 12/2004 | Donnelly et al. | 606/232 |
| 2004/0260298 A1 * | 12/2004 | Kaiser et al. | 606/72 |
| 2005/0038427 A1 | 2/2005 | Perriello et al. | |
| 2005/0090827 A1 * | 4/2005 | Gedebou | 606/72 |
| 2005/0234460 A1 | 10/2005 | Miller | |
| 2005/0240189 A1 | 10/2005 | Rousseau et al. | |
| 2005/0267479 A1 * | 12/2005 | Morgan et al. | 606/73 |
| 2005/0273138 A1 * | 12/2005 | To et al. | 606/219 |
| 2005/0277961 A1 | 12/2005 | Stone et al. | |
| 2005/0288710 A1 | 12/2005 | Fallin et al. | |
| 2006/0052786 A1 | 3/2006 | Dant et al. | |
| 2006/0122608 A1 * | 6/2006 | Fallin et al. | 606/72 |
| 2006/0241656 A1 * | 10/2006 | Starksen et al. | 606/143 |
| 2006/0265011 A1 * | 11/2006 | Bonutti | 606/232 |
| 2006/0276841 A1 * | 12/2006 | Barbieri et al. | 606/232 |
| 2006/0282081 A1 * | 12/2006 | Fanton et al. | 606/72 |
| 2006/0282082 A1 * | 12/2006 | Fanton et al. | 606/72 |
| 2007/0010794 A1 | 1/2007 | Dann et al. | |
| 2007/0016208 A1 | 1/2007 | Thornes | |
| 2007/0049944 A1 * | 3/2007 | Stone et al. | 606/72 |
| 2007/0100353 A1 | 5/2007 | Chudik | |
| 2007/0112338 A1 | 5/2007 | Cohen et al. | |
| 2007/0118132 A1 * | 5/2007 | Culbert et al. | 606/72 |
| 2007/0142835 A1 | 6/2007 | Green et al. | |
| 2007/0225719 A1 * | 9/2007 | Stone et al. | 606/72 |
| 2007/0233241 A1 | 10/2007 | Graf et al. | |
| 2007/0270857 A1 | 11/2007 | Lombardo et al. | |
| 2008/0046009 A1 | 2/2008 | Albertorio et al. | |
| 2008/0086138 A1 | 4/2008 | Stone et al. | |
| 2008/0109038 A1 * | 5/2008 | Steiner et al. | 606/232 |
| 2008/0188935 A1 | 8/2008 | Saylor et al. | |
| 2008/0255613 A1 * | 10/2008 | Kaiser et al. | 606/232 |
| 2008/0287991 A1 * | 11/2008 | Fromm | 606/232 |
| 2009/0018654 A1 | 1/2009 | Schmieding et al. | |
| 2009/0105754 A1 * | 4/2009 | Sethi | 606/228 |
| 2009/0204146 A1 * | 8/2009 | Kaiser et al. | 606/228 |
| 2009/0234387 A1 * | 9/2009 | Miller et al. | 606/232 |
| 2010/0004683 A1 * | 1/2010 | Hoof et al. | 606/232 |
| 2010/0063541 A1 * | 3/2010 | Brunelle et al. | 606/232 |
| 2010/0262185 A1 * | 10/2010 | Gelfand | A61B 17/0401 |
| | | | 606/232 |

(56) References Cited

U.S. PATENT DOCUMENTS

| | | | |
|---|---|---|---|
| 2010/0268273 A1* | 10/2010 | Albertorio et al. | 606/232 |
| 2011/0054526 A1* | 3/2011 | Stone et al. | 606/232 |
| 2011/0125189 A1 | 5/2011 | Stoll, Jr. et al. | |
| 2011/0208194 A1 | 8/2011 | Steiner et al. | |
| 2011/0224764 A1* | 9/2011 | Kulle | 607/116 |
| 2011/0238113 A1* | 9/2011 | Fanton et al. | 606/232 |
| 2011/0301708 A1* | 12/2011 | Stone et al. | 623/13.14 |
| 2012/0116452 A1* | 5/2012 | Stone et al. | 606/232 |
| 2012/0180291 A1 | 7/2012 | Oren et al. | |
| 2013/0023929 A1* | 1/2013 | Sullivan et al. | 606/232 |
| 2013/0090687 A1* | 4/2013 | Lebeau | A61B 17/0401 606/232 |
| 2013/0103085 A1* | 4/2013 | Hart et al. | 606/232 |
| 2013/0123843 A1* | 5/2013 | Chan et al. | 606/232 |
| 2013/0131723 A1* | 5/2013 | Snell et al. | 606/232 |
| 2013/0238025 A1* | 9/2013 | Howard et al. | 606/232 |
| 2013/0253581 A1* | 9/2013 | Robison | 606/232 |
| 2013/0268073 A1* | 10/2013 | Albertorio et al. | 623/13.12 |
| 2013/0304120 A1* | 11/2013 | Stone et al. | 606/232 |
| 2013/0331885 A1* | 12/2013 | Stone et al. | 606/232 |
| 2013/0338710 A1* | 12/2013 | Heaven et al. | 606/232 |
| 2014/0025110 A1* | 1/2014 | Bonutti et al. | 606/232 |
| 2014/0194927 A1* | 7/2014 | Kaiser et al. | 606/232 |
| 2016/0166297 A1* | 6/2016 | Mighell | A61B 17/8057 606/291 |
| 2016/0235398 A1* | 8/2016 | Nguyen | A61B 17/0401 |
| 2016/0302785 A1* | 10/2016 | Nason | A61B 17/0401 |

OTHER PUBLICATIONS

Orthopedics Today, Point/Counterpoint ACL Reconstruction, Mar. 7, 2008.
Smith & Nephew, Endobutton CL, Fixation System, Knee Series, Technique Guide, 1999.
European Search Report, EP 12150748, May 8, 2012.
Supplementary European Search Report for EP Appln. No. 08837097.8—Dated Sep. 22, 2016.

* cited by examiner

TOGGLE BOLT ASSEMBLY AND METHOD OF ASSEMBLY

CROSS-REFERENCE TO RELATED APPLICATIONS

This application claims the benefit of the filing date of U.S. Provisional Patent Application No. 61/432,481 filed Jan. 13, 2011, the disclosure of which is hereby incorporated herein by reference.

BACKGROUND OF THE INVENTION

The use of continuous closed suture loops has been incorporated in soft tissue surgeries in recent years, particularly since the proliferation of the use of knotless anchors. The decrease in the number of knots needed in a surgery is important as there is always a chance a knot may come undone or that the knot creates an area of higher incidence of suture breakage.

However, the use of continuous closed suture loops and the like presents unique manufacturing challenges, particularly in how to secure a continuous closed suture loop to a structure. One known method includes forming the continuous closed suture loop directly on the structure, such that a length of suture is passed through the structure, and is then braided or secured to form a continuous closed suture loop, while still positioned on the structure. Of course, such a method presents numerous difficulties, particularly in a situation where the suture and the structure are made in separate locations, or by separate entities, such that it would not be possible to sew the suture loop onto the structure without added shipping costs and lead time in preparing a final product.

BRIEF SUMMARY OF THE INVENTION

In a first embodiment, the present invention includes a method of assembling an anchor for use in tissue comprising an anchor body, a continuous closed suture loop and an insert, the method may include positioning a portion of the continuous closed suture loop through an opening in the anchor body; positioning the insert adjacent the portion of the continuous closed suture loop which was passed through the opening; and securing the insert to the anchor body such that the continuous closed suture loop is secured to the anchor body by the insert.

The method of assembly may further include the steps of sterilizing the assembled anchor and packaging the assembled anchor. Furthermore, the anchor body and insert may be secured to one another using a snap-fit connection, though other connections such as male/female threaded, press-fit, screw, bolt or rivet, welding, and the like are also envisioned.

Additional elements which may be included on the tissue anchor include an additional suture, a flexible rod and rod connector, and the like. Further, the opening may be a bore hole, and the anchor body may further include an additional bore hole for passage of an additional suture or lead suture. The insert may also include a saddle which is shaped to generally mimic the path of the continuous closed suture loop within the saddle once the loop undergoes tension from an attached soft tissue, wherein the portion of the continuous closed suture loop is positioned on the saddle.

In another embodiment, the method of assembling an anchor assembly for use in tissue, wherein the anchor includes an anchor body, a continuous closed suture loop, an insert, and a connector, the method may include securing the connector to the anchor body; positioning a portion of the continuous closed suture loop through an opening in the anchor body; positioning the insert adjacent the portion of the continuous closed suture loop which was passed through the opening; and securing the insert within the opening such that the continuous closed suture loop may be secured to the anchor body by the insert. The anchor may also include an insertion device and a lead suture. The method may further include the steps of securing an insertion device (such as a flexible rod) to the connector and/or passing a lead suture through a bore hole in the anchor body. The steps of securing the connector to the anchor body, securing the insertion device to the connector and passing the lead suture through the bore hole in the anchor body may be performed at any time during the assembly of the anchor for use in tissue.

Further, insert may include a saddle shaped to generally mimic the path of the continuous closed suture loop within the saddle once the loop undergoes tension from an attached soft tissue, wherein the continuous closed suture loop is positioned within the saddle. The saddle and anchor body may secure to one another through one of a press-fit connection, a snap-fit connection, a male and female threaded connection, at least one screw, bolt or rivet, a weld, or the like.

In any of the embodiments, the continuous closed suture loop may include a length which may be adjustable or fixed.

BRIEF DESCRIPTION OF THE DRAWINGS

FIG. 3A is an isometric view and FIG. 3B is an end view of the embodiment of FIG. 3A.

DETAILED DESCRIPTION

Figure 1:
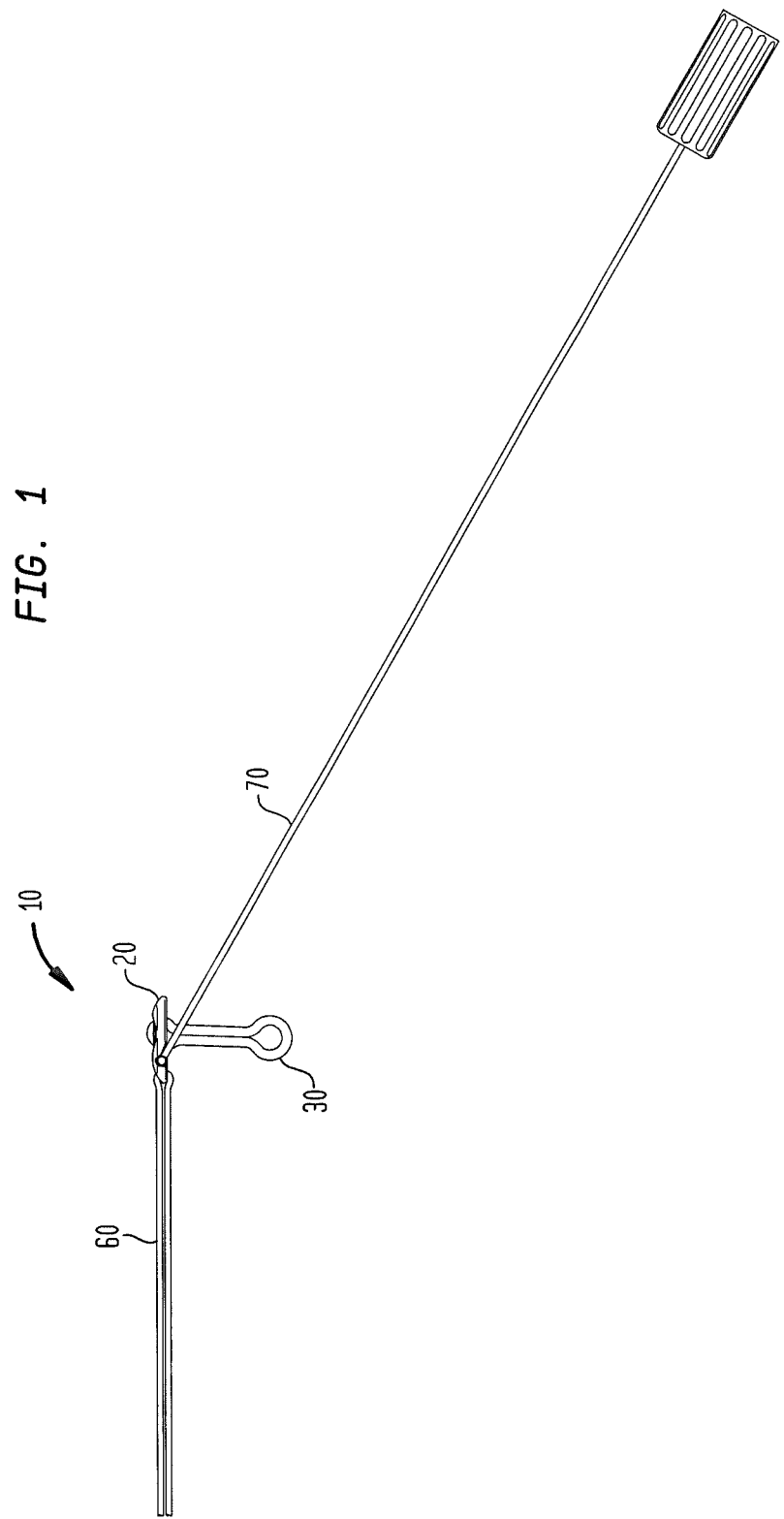
FIG. 1 illustrates a first embodiment tissue anchor and inserter assembly.
Figure 2:
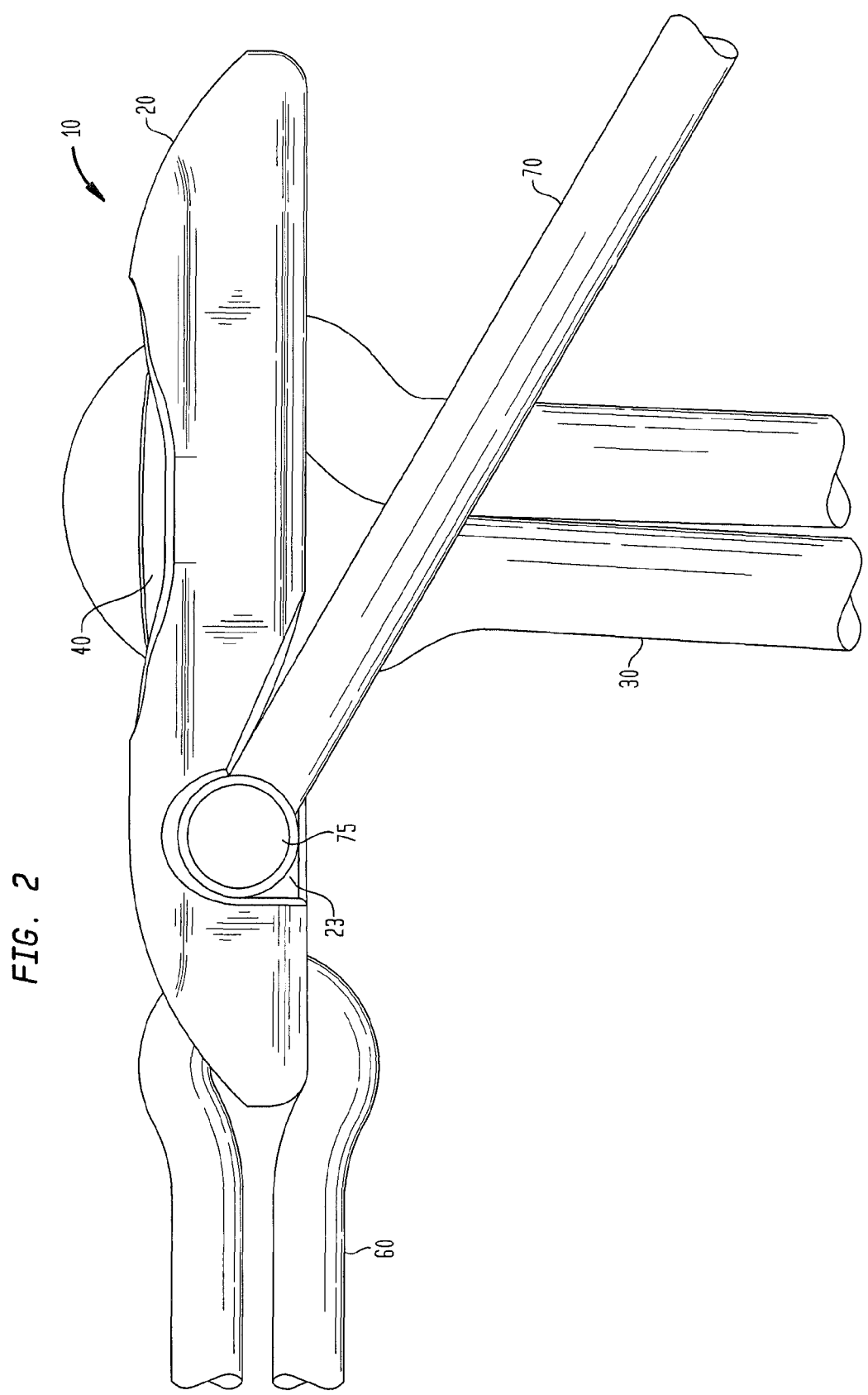
FIG. 2 illustrates the assembly of FIG. 1 and the connection between the tissue anchor and the inserter.
Figure 3A:
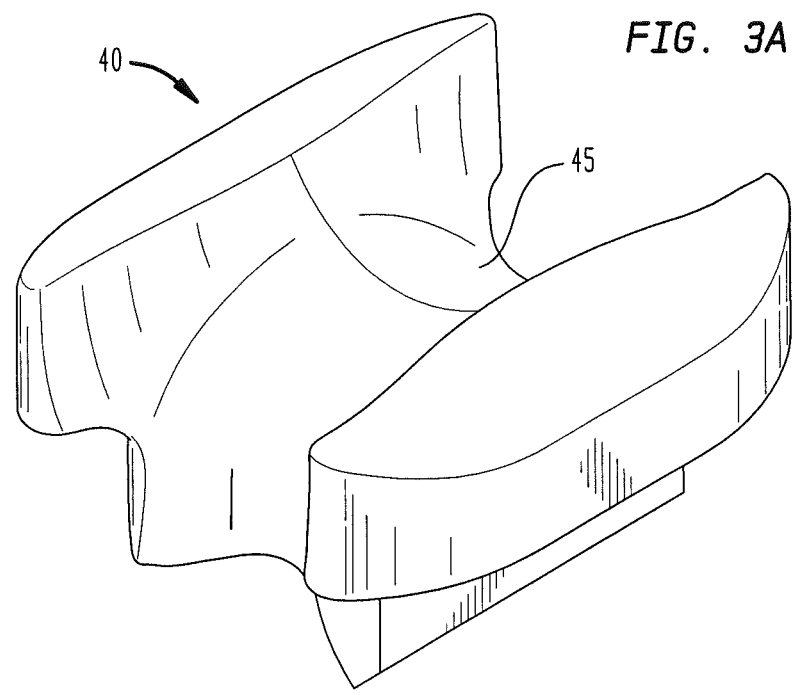
FIGS. 3A and 3B illustrate one embodiment of an insert for use in the tissue anchor.
Figure 3B:
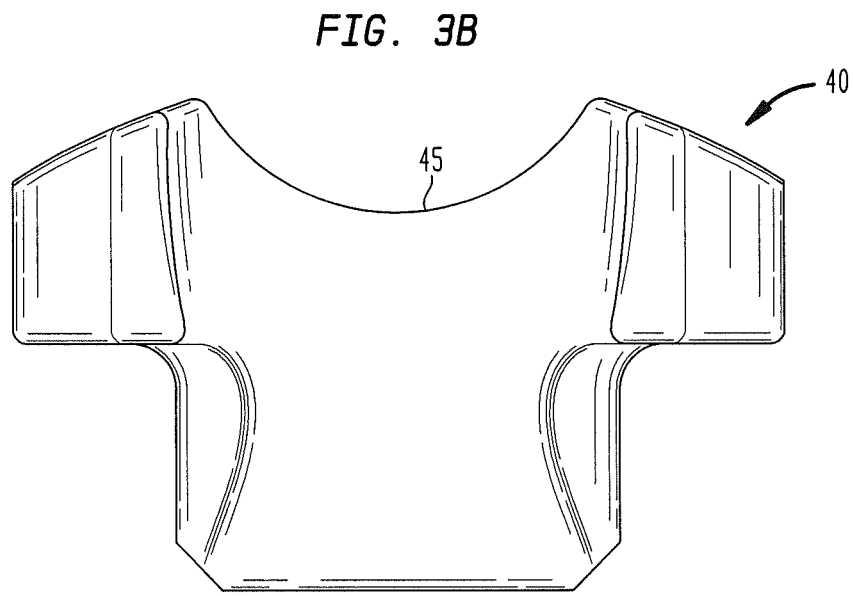
Figure 4A:
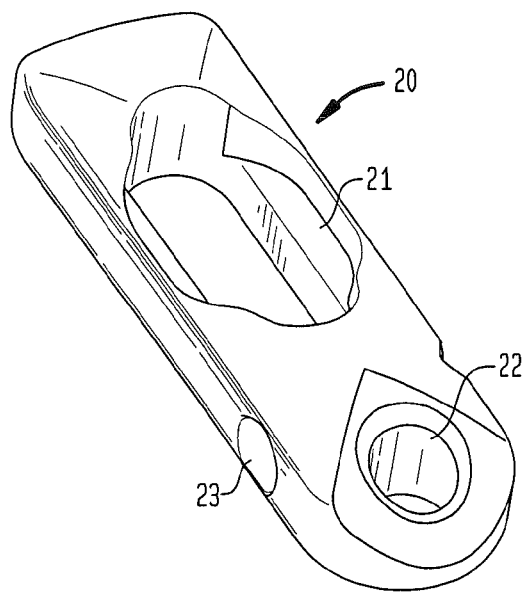
FIG. 4A illustrates one embodiment of an anchor body.
Figure 4B:
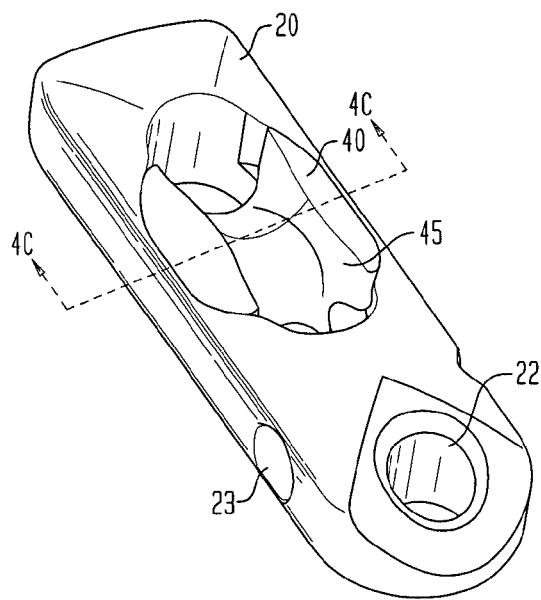
FIG. 4B illustrates the anchor body of FIG. 4A with the insert of FIGS. 3A and 3B positioned therein.
Figure 4C:
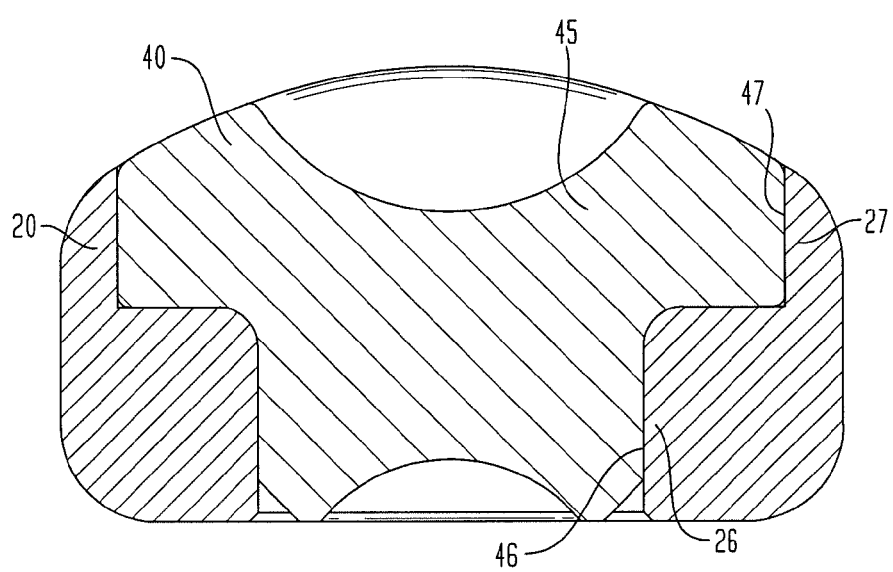
FIG. 4C illustrates a cross-section of FIG. 4B.

The present invention includes a method of assembly of a tissue anchor and method of manufacture thereof. While this application may cover any type of tissue anchor which requires the use of a continuous closed suture loop, the following will be focused on a toggle button anchor for use in soft tissue repair, such as ACL replacement surgery where the toggle button anchor may secure an ACL graft within a bone tunnel in the femur. Such a toggle anchor is disclosed in pending U.S. application Ser. No. 12/682,324, entitled Toggle Bolt Suture Anchor Kit, filed on Apr. 9, 2010 as a U.S. National Phase of PCT Application No. US2008079277, the disclosure of which is incorporated by reference herein as if fully set forth herein. One example of preparation of a knee joint for ACL replacement, including the preparation of a femoral tunnel within which the ACL graft will be secured, is disclosed in U.S. application Ser. No. 12/859,580, entitled Flexible ACL Instrumentation, Kit And Method, the disclosure of which is incorporated by reference herein as if fully set forth herein. Alternatively, the tissue anchor of this invention may be used in other soft or hard tissue repairs such as meniscus repair, other tendon or ligament repair, or in bone repair, e.g., securing bone fragments together after a fracture of the bone, or the like. For ease of illustration, the exemplary use in this application will be ACL repair in which a replacement ACL graft is secured within a bone tunnel.

The tissue anchor 10, as illustrated in FIGS. 1, 2 and 5-7, includes an anchor body 20, a continuous closed suture loop 30, and an insert 40. The tissue anchor 10 may further include a lead suture 60, and a flexible rod inserter 70 and connector 75.

The anchor body 20 may include an opening, such as bore hole 21, which is generally oval in shape, though other shapes may be used as well. The body 20 may also have a second bore hole 22 and a groove 23 through which the lead suture 60 and connector 75 may be positioned, respectively. The anchor body 20 may be constructed of plastic such as PEEK, metal such as titanium, ceramic, or the like. The anchor body 20 may be manufactured using known molding or machining processes commonly used with such materials.

The continuous closed suture loop 30 may be any suture loop capable of securing a graft to the anchor body 20 without causing damage or unnecessary stress to the graft (not shown) which may be looped through suture loop 30 or otherwise secured thereto. The diameter of the suture loop may be of any dimension, for example, between about 0.5 mm to about 5.0 mm, depending on the anticipated use of the tissue anchor 10. For example, if the anchor is to be used for ACL fixation, the diameter may be from about 1.0 mm to about 5.0 mm, though if the anchor 10 is to be used in rotator cuff repair, the diameter may be from about 0.5 mm to about 5.0 mm. The length of the suture loop 30 may also be dependent upon the anticipated use. For example, in ACL replacement surgery, using the tissue anchor 10 to secure the ACL graft to the femur, the length of the suture loop 30, measured when the suture loop 30 is gently pulled at opposite ends, may be from about 10 mm to about 50 mm. Further as to this example, a series of anchor bodies 20 and suture loop 30 combinations may be offered in about 5 mm increments, such that the offered range may be a 10 mm loop, 15 mm loop, 20 mm loop and so on up to a 50 mm loop. These various length suture loops may be provided in a kit. Alternatively, the anchor body 20 may be alone and without a suture loop 30. The continuous closed suture loop may be manufactured from ultra high molecular weight polyethylene or other like material suitable for approximation of a tissue graft such as a replacement ACL. In an alternative arrangement, the continuous closed suture loop may be adjustable such that, for example, the loop may have a length of about 50 mm, but the loop may be tightened such that the length can be shortened to about 10 mm. In this arrangement, a kit may not be necessary, but instead, a single adjustable continuous loop may be adjusted by the user to obtain the desired length of suture loop for the anticipated procedure.

As illustrated in FIGS. 2-7, the insert 40 may be constructed from the same material as the anchor body 20, though it may also be made of a different material, so long as the two materials are compatible with one another with regards to strength (to maintain a rigid connection, as discussed below), as well as chemically (the two materials do not adversely react to one another). As illustrated in FIGS. 3A and 3B, the insert may include a saddle 45 which is dimensioned such that the continuous closed suture loop 30 fits within the saddle. Specifically, the saddle 45 may be, for example, curved in two different directions to match the diameter of the suture loop and the curve of the suture itself. Thus, the saddle may generally mimic the path of the continuous closed suture loop 30 such that it will apply minimal strains to the loop 30 once tension is applied to the attached soft tissue, for example, the ACL graft.

The insert 40 and anchor body 20 may be capable of being secured to one another, such that the continuous closed suture loop 30 is secured to the anchor body 20 via the insert 40. In one embodiment, illustrated in FIGS. 4A-4C, the insert and anchor body may include a matching press-fit connection, including a male portion 46 and 47 on the insert and a female portion 26, 27 on the anchor body. The respective male and female portions (46 and 26; 47 and 27) can contact one another and create a pressure fit which maintains the insert within the bore hole 21 of the anchor body. Of course, other connections may be used as well, such as a male/female threaded connection, a snap-fit connection (i.e., rib and groove connection), the use of screws, bolts or rivets, a permanent connection such as a weld, an adhesive, or the like. Additionally, once installed at a surgical site, and thus once tension is applied to the suture loop, the insert will also be held in place by the suture loop itself as the force applied to the suture loop by the graft will force the insert to remain within the bore hole 21. As such, in one embodiment, the press-fit connection may be merely sufficient to hold the insert in place within the bore hole 21 after manufacture but prior to implantation, and then, upon implantation, the tension of the tissue graft on the suture loop may assist in maintaining the insert within the bore hole.

The press-fit, or other connection, is intended to maintain the continuous closed suture loop 30 in connection with anchor body 20 once the anchor body and insert are coupled together during manufacture. Regardless of the connection, once assembled, the insert 40 should not be removed from the anchor body 20, and as such the connection used should be substantially rigid and as such, difficult to reverse. Of course, the connection used may be capable of being separated if a particular use of the tissue anchor 10 is envisioned and separating the elements of the tissue anchor 10 is beneficial, such as in the example of a kit supplied to a surgeon which includes at least one anchor and a plurality of continuous closed suture loops which are intended to be combined by the surgeon. In most situations, however, the tissue anchor 10 is intended to remain as a single device and the various elements need not be separated from one another. In the above example of various suture loop lengths forming a kit, it is envisioned that the anchor body and insert may be separated to install a desired length suture loop or, alternatively, the kit includes a plurality of anchors with each suture loops pre-installed, at manufacture.

In an alternative arrangement, the insert may instead be connected to the anchor body 20 by approaching from the side of the anchor body and coupling to the anchor body within an opening on the side of the anchor body. In yet another alternative, the anchor body may have a structure on its bottom face which may accept the insert, approaching from the bottom of the anchor body. Thus, the insert and anchor body may be connected together in other arrangements than as illustrated herein so long as the two structures are capable of securing a continuous suture loop to the anchor body.

The flexible rod inserter 70 may be removably secured to the anchor body 20 through connector 75, which is itself secured to the anchor body 20 within groove 23. Groove 23 may be of any shape suitable to secure connector 75 therein. The connector 75 may be pivotable within groove 23, to assist in the rotation of anchor body 20 relative to rod inserter 70. The connection between the connector 75 and rod inserter 70 may be a threaded connection, a taper connection, a snap-fit connection, a press-fit connection, or the like such that the rod inserter 70 may be removed from the anchor body 20 once the anchor body is in place at the desired anatomical site.

Figure 5:
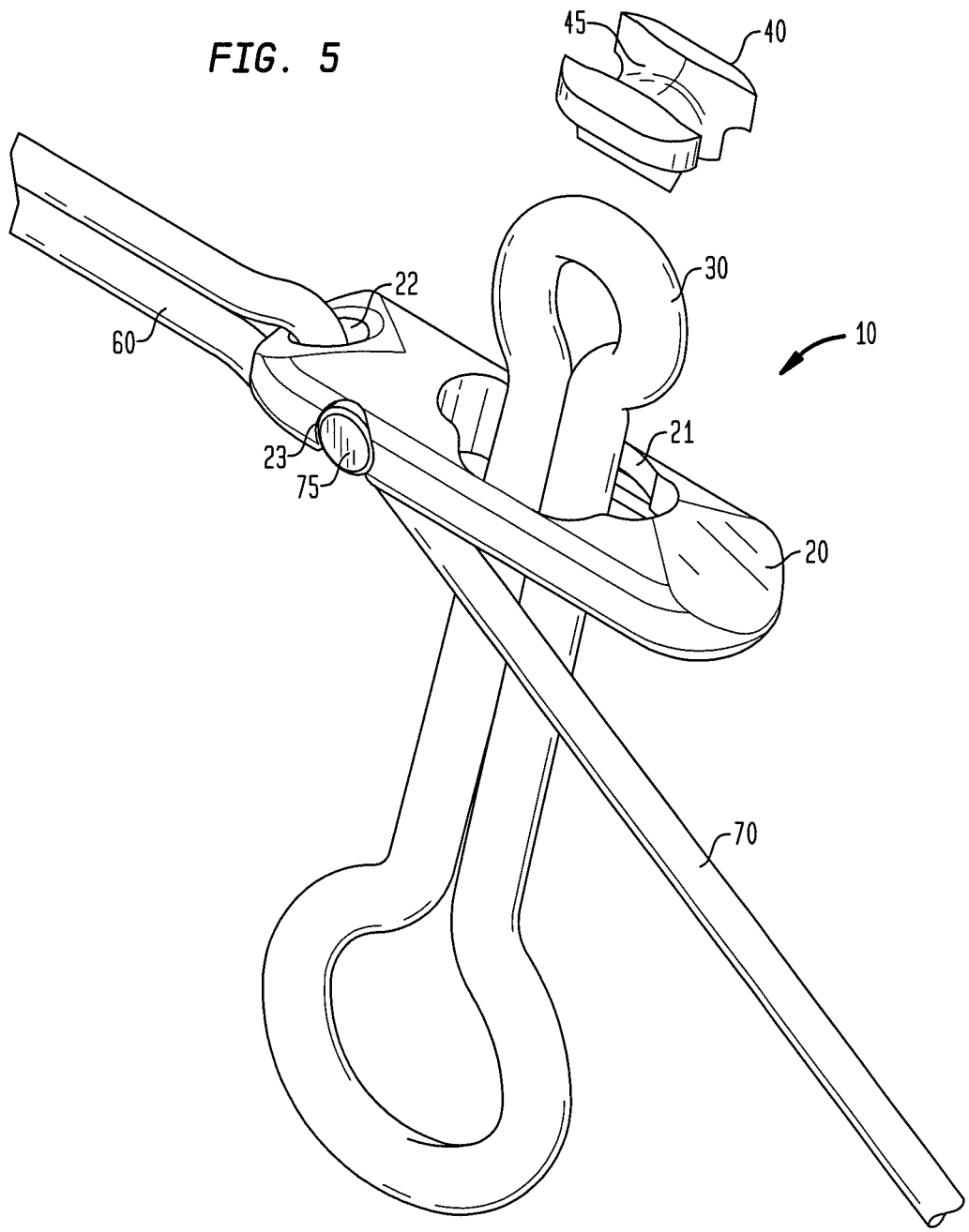
FIG. 5 illustrates a first embodiment tissue anchor wherein a continuous closed suture loop is passed through an opening in an anchor body.
Figure 6:
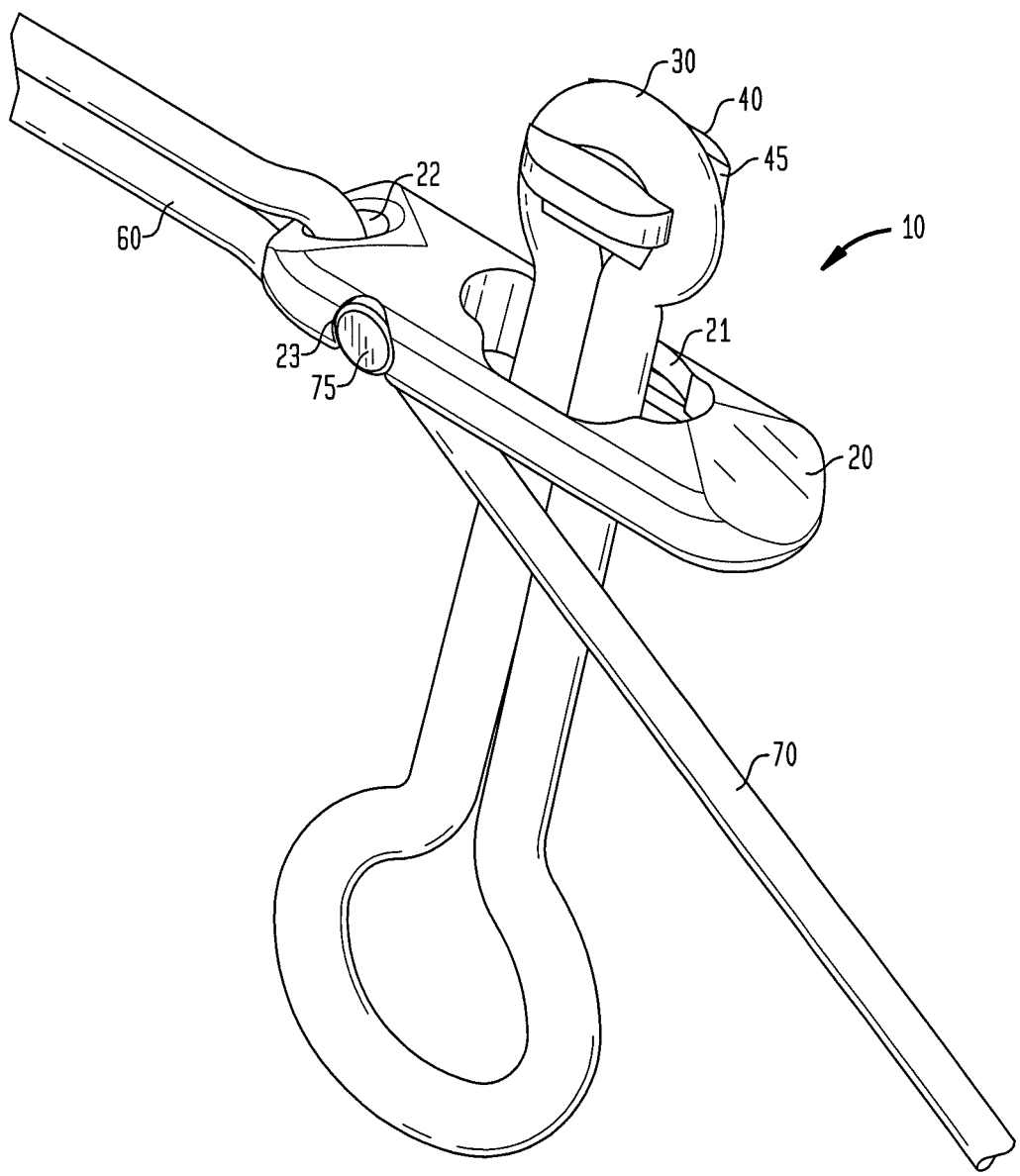
FIG. 6 illustrates the embodiment of FIG. 1, wherein a saddle of an insert is positioned adjacent a portion of the continuous closed suture loop.
Figure 7:
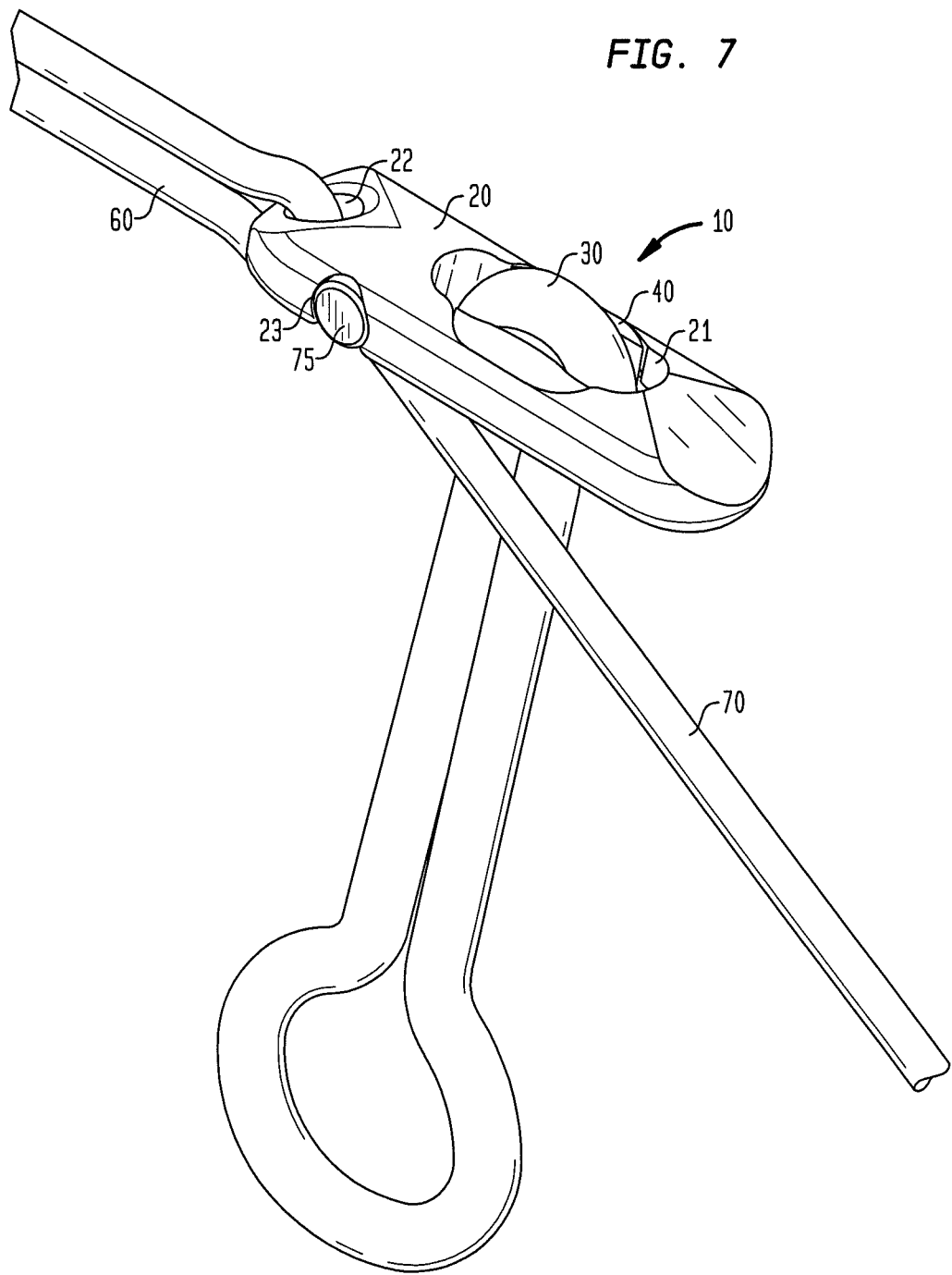
FIG. 7 illustrates the embodiment of FIGS. 1 and 2, wherein the insert is secured within the opening of the anchor body to secure the continuous closed suture loop to the anchor body.

In a first embodiment of the method of assembly of the tissue anchor 10, the method may include, as illustrated in FIG. 5, positioning a portion of the continuous closed suture loop 30 through the bore hole 21 in the anchor body 20. Next, as illustrated in FIG. 6, the insert 40 having a saddle 45 may be positioned adjacent the portion of the continuous closed suture loop 30 which was passed through the bore hole 21, such that the continuous closed suture loop may be positioned within the saddle. Finally, as illustrated in FIG. 7, the insert 40 may be secured within the bore hole 21 such that the continuous closed suture loop 30 is secured to the anchor body 20 by the insert 40. The insert 40 may be secured to the anchor body 20 through a connection, such as the snap-fit, press-fit or other connection, as was illustrated in FIG. 4. Additional steps including placement of the lead suture 60, and the flexible rod inserter 70 and connector 75 may be performed at any time throughout this method of assembly. For example, the connector 75 may be secured to the anchor body 20 first, before the continuous closed suture loop 30 is introduced. Additionally, once the suture loop 30 is secured to the anchor body 20, the lead suture 60 may be passed through a second bore hole in the anchor body 20 and the flexible rod inserter 70 may be secured to the anchor body 20 via the connector 75.

Such a method of assembly may provide cost savings and time savings needed for assembly. For example, if one manufacturing plant, or one company, in one location manufactured the continuous closed suture loop 30, and a second plant, or company, in a second location manufactured the anchor body 20 and insert 40, the assembly of the tissue anchor 10 may then be completed at the second plant or company by having the first plant or company send the finished suture loop 30 to the second location to be assembled to the anchor body 20. This minimizes shipping costs related to, for example, the second company sending a one-piece tissue anchor to the first company, having the first company braid a suture loop onto the anchor, and then sending the completed anchor with suture loop back to the second company for final assembly of other parts, etc. and final shipment to the customer.

The assembly method of this application also provides for ease of sterilization in that the entire tissue anchor 10 may be assembled in a single location, and thus can be sterilized at that location and packaged for distribution at that single location as well.

Such an assembly method provides the additional benefit of eliminating the step of braiding the suture loop directly onto the tissue anchor, which can be difficult for a machine or individual to accomplish. Instead, the suture loop may be prepared in a normal fashion without the hindrance of the tissue anchor being present. The continuous closed suture loop may then be secured to the tissue anchor, using the insert, without tying any knots.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of assembling a toggle button anchor for use in securing tissue comprising an anchor body, a continuous closed suture loop and an insert having a saddle and a bottom surface opposite the saddle, the method comprising:
   receiving a portion of the continuous closed suture loop through an opening in the anchor body, the anchor body including a length between a first end and a second end, a top surface, a bottom surface, and the opening positioned transverse to the length and extending from the top surface to the bottom surface;
   receiving the insert adjacent the portion of the continuous closed suture loop which was received through the opening such that the portion of the continuous closed suture loop which was passed through the opening is positioned on the insert; and
   securing the insert to the anchor body by placing the insert into an end of the opening defined by the top surface such that the insert bottom surface is at least partially co-planar with the anchor body bottom surface, thereby securing the continuous closed suture loop to the anchor body via the insert, wherein the saddle includes a saddle surface extending in the direction of the length of the body from a first end of the saddle to a second end of the saddle, and the portion of the continuous closed suture loop contacts the saddle surface once the loop undergoes tension from an attached soft tissue.

2. The method of claim 1, wherein the saddle and anchor body secure to one another through a press-fit connection.

3. The method of claim 1, wherein the method of assembling further comprises, prior to positioning the continuous closed suture loop through the opening, securing a connector for an insertion device to the anchor body.

4. The method of claim 3, wherein the insertion device is connected to the connector after the insert is secured to the anchor body.

5. The method of claim 4, wherein the insertion device is a flexible rod.

6. The method of claim 1, further comprising, after the step of securing the insert to the anchor body, passing a lead suture through a bore hole in the anchor body.

7. The method of claim 1, further comprising the step of sterilizing the anchor.

8. The method of claim 1, further comprising the step of packaging the anchor as a completed assembly.

9. The method of claim 1, wherein the continuous closed suture loop has an adjustable length.

10. The method of claim 1, wherein the insert and opening have similar cross-sectional shapes.

11. The method of claim 1, wherein an upper portion of the enclosed opening has a first width and a lower portion of the enclosed opening has a second width, and a contact surface positioned between the first width and the second width, wherein the first width is greater than the second width.

12. A method of assembling a toggle button anchor assembly for use in securing tissue comprising an elongated anchor body having a longitudinal axis along a length thereof and an enclosed opening extending through the anchor body in a direction transverse to the longitudinal axis, a continuous closed suture loop, and an insert having an insert top surface, wherein the anchor body has a first surface and a second surface on an opposite side of the enclosed opening which together form an anchor body top surface, the method comprising:

receiving a portion of the continuous closed suture loop through the enclosed opening in the anchor body;

receiving the insert in the anchor body in the direction transverse to the longitudinal axis and adjacent to the portion of the continuous closed suture loop which was received through the enclosed opening by contacting the insert with the continuous closed suture loop to pull the insert into the enclosed opening; and securing the insert within the enclosed opening by using the continuous closed suture loop such that the continuous closed suture loop is secured to the anchor body via the insert.

13. The method of assembly of claim 12, wherein the insert comprises a saddle which includes a surface from a first end of the saddle to a second end of the saddle, and the portion of the continuous closed suture loop contacts the surface from the first end to the second end once the loop undergoes tension from an attached soft tissue.

14. The method of claim 12, further comprising the step of sterilizing the anchor body.

15. The method of claim 12, further comprising the step of securing a connector to the anchor body.

16. The method of claim 15, wherein the step of securing the connector to the anchor body is performed prior to the step of positioning a portion of the continuous closed suture loop through the enclosed opening in the anchor body.

17. The method claim 15, further comprising the step of securing an insertion device to the connector.

18. The method of claim 17, wherein the step of securing the insertion device to the connector is performed after the step of securing the insert within the opening.

19. The method of claim 17, further comprising the step of passing a lead suture through a bore hole in the anchor body.

20. The method of claim 19, wherein the step of passing a lead suture through the bore hole in the anchor body is performed after the step of securing the insertion device to the connector.

21. The method of claim 12, wherein the insert comprises a lower portion having a lower portion base defining a first perimeter and an upper portion having an upper portion base defining a second perimeter greater than the first perimeter, in which, when the insert is secured within the enclosed opening of the anchor body, the upper and lower portion bases are located within the anchor body.

22. The method of claim 21, wherein, when the insert is secured within the enclosed opening of the anchor body, the upper portion base of the insert rests on a step within the anchor body.

23. The method of claim 12, wherein the insert top surface is flush with an edge defining the enclosed opening of the anchor body, the insert top surface facing away from the anchor body.

24. The method of claim 12, wherein insert top surface forms an uninterrupted surface with the first and second surfaces of the anchor body, the insert top surface facing away from the anchor body.

25. The method of claim 12, further comprising securing the insert within the enclosed opening such that an insert bottom surface opposite the insert top surface is co-planar with at least a portion of an anchor body bottom surface opposite the anchor body top surface, wherein the insert bottom surface faces away from the anchor body.

26. A method of assembling a toggle button anchor assembly for use in securing tissue comprising an elongated anchor body having a longitudinal axis along a length thereof and an enclosed opening extending through the anchor body in a direction transverse to the longitudinal axis, a continuous closed suture loop, and an insert including a lower portion having a lower portion base defining a first perimeter and an upper portion having an upper portion base defining a second perimeter greater than the first perimeter, wherein the anchor body has a first surface and a second surface on an opposite side of the enclosed opening which together form an anchor body top surface, the method comprising:

receiving a portion of the continuous closed suture loop through the enclosed opening in the anchor body;

receiving the insert in the anchor body in the direction transverse to the longitudinal axis and adjacent to the portion of the continuous closed suture loop which was received through the enclosed opening; and securing the insert within the enclosed opening such that the continuous closed suture loop is secured to the anchor body via the insert and the upper portion base of the insert rests on a stepped portion within the anchor body.

27. A method of assembling a toggle button anchor assembly for use in securing tissue comprising an elongated anchor body having a longitudinal axis along a length thereof and an enclosed opening extending through the anchor body in a direction transverse to the longitudinal axis, a continuous closed suture loop, and an insert, wherein the anchor body has a first surface and a second surface on an opposite side of the enclosed opening which together form an anchor body top surface, the method comprising:

receiving a portion of the continuous closed suture loop through the enclosed opening in the anchor body;

receiving the insert in the anchor body in the direction transverse to the longitudinal axis and adjacent to the portion of the continuous closed suture loop which was received through the enclosed opening; and securing the insert within the enclosed opening such that the continuous closed suture loop is secured to the anchor body via the insert through one of a press-fit connection, a male and female threaded connection, at least one separate fastener, and a weld.

* * * * *